US012106858B2

(12) United States Patent
Dessaud et al.

(10) Patent No.: US 12,106,858 B2
(45) Date of Patent: Oct. 1, 2024

(54) SYSTEM AND METHOD THAT OPTIMIZES PHYSICAL ACTIVITY RECOMMENDATIONS BASED ON RISKS OF FALLS

(71) Applicant: KONINKLIJKE PHILIPS N.V., Eindhoven (NL)

(72) Inventors: Nathalie Magali Danielle Dessaud, Wintelre (NL); Janneke Annegarn, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 505 days.

(21) Appl. No.: 17/253,459

(22) PCT Filed: Jun. 27, 2019

(86) PCT No.: PCT/EP2019/067271
§ 371 (c)(1),
(2) Date: Dec. 17, 2020

(87) PCT Pub. No.: WO2020/002566
PCT Pub. Date: Jan. 2, 2020

(65) Prior Publication Data
US 2021/0125728 A1    Apr. 29, 2021

Related U.S. Application Data

(60) Provisional application No. 62/691,794, filed on Jun. 29, 2018.

(51) Int. Cl.
*G16H 50/30*    (2018.01)
*A61B 5/00*    (2006.01)
(Continued)

(52) U.S. Cl.
CPC ............. *G16H 50/30* (2018.01); *A61B 5/024* (2013.01); *A61B 5/1117* (2013.01);
(Continued)

(58) Field of Classification Search
CPC ...... G16H 20/30; G16H 50/30; A61B 5/1117; A61B 5/7264–7275; A61B 5/7282
See application file for complete search history.

(56) References Cited

U.S. PATENT DOCUMENTS

2012/0165703 A1 * 6/2012 Bottum ................. G16H 20/30
600/595
2014/0083490 A1    3/2014 Sharma et al.
(Continued)

FOREIGN PATENT DOCUMENTS

JP    2009261595 A  * 11/2009
WO   WO-2010009278 A2 *  1/2010  ......... G06F 19/3475
(Continued)

OTHER PUBLICATIONS

Marston et al., The design of a purpose-built exergame for fall prediction and prevention for older people, 2015, European Review of Aging and Physical Activity (Year: 2015).*
(Continued)

*Primary Examiner* — Karen A Hranek (57) ABSTRACT

Techniques are described herein for incorporating fall prevention into a personalized activity plan. In various embodiments, a baseline risk of fall for a user may be estimated (302) based on baseline sensor signal(s) (203, 205, 207). Based on a prediction model (215) (which may/may not be associated with the user) and the baseline risk of fall, respective risks of falls associated with various candidate activities may be predicted (304), and then candidate activities may be determined or selected (306) based on the predicted respective risks of falls. Output indicative of the determined candidate activities may be provided (308) to the user, who may provide input (310) identifying one or more of the determined candidate activities as an exercise conducted or to be conducted by the user. Based on the exercise
(Continued)

sensor signal(s), a subsequent risk of fall for the user may be estimated (312) and used to update (314) the prediction model.

15 Claims, 4 Drawing Sheets

(51) Int. Cl.
*A61B 5/024* (2006.01)
*A61B 5/11* (2006.01)
*G16H 20/30* (2018.01)
*G16H 50/20* (2018.01)

(52) U.S. Cl.
CPC ........... *A61B 5/7275* (2013.01); *G16H 20/30* (2018.01); *G16H 50/20* (2018.01)

(56) References Cited

U.S. PATENT DOCUMENTS

| | | | |
|---|---|---|---|
| 2015/0012284 A1* | 1/2015 | Schenk | G16H 20/30 705/2 |
| 2015/0374281 A1* | 12/2015 | Breuille | A61B 5/486 600/595 |
| 2016/0113551 A1 | 4/2016 | Annegarn et al. | |
| 2016/0220153 A1 | 8/2016 | Annegarn et al. | |
| 2016/0310791 A1* | 10/2016 | Fauci | A61B 5/02433 |
| 2017/0000387 A1* | 1/2017 | Forth | G06N 7/01 |
| 2017/0151081 A1* | 6/2017 | Feris | A61F 5/0102 |
| 2017/0213145 A1 | 7/2017 | Pathak et al. | |
| 2017/0273601 A1* | 9/2017 | Wang | A61B 5/1118 |
| 2017/0323582 A1* | 11/2017 | Nusbaum | G09B 19/0092 |
| 2018/0177436 A1 | 6/2018 | Chang et al. | |
| 2019/0175988 A1* | 6/2019 | Volterrani | A63B 22/0605 |
| 2019/0254569 A1* | 8/2019 | Asada | A61B 5/742 |

FOREIGN PATENT DOCUMENTS

| | | | | |
|---|---|---|---|---|
| WO | WO-2010041001 A1 * | 4/2010 | | A63B 21/00 |
| WO | 2014083490 A1 | 6/2014 | | |
| WO | 2014195146 A1 | 12/2014 | | |
| WO | WO-2018127506 A1 * | 7/2018 | | A61B 5/1117 |

OTHER PUBLICATIONS

Shier et al., Implementing exercise programs to prevent falls: systematic descriptive review, 2016, Injury Epidemiology (Year: 2016).*
Ho et al., Decision Combination in Multiple Classifier Systems, Jan. 1994, IEEE Transactions on Patterns ANalysis and Machine Intelligence vol. 16 No. 1 (Year: 1994).*
Krause et al., AN Ensemble of Classifiers Approach for the Missing Feature Problem, 2003, IEEE (Year: 2003).*
Radu et al., Multimodal Deep Learning ofr Activity and Context Recognition, Dec. 2017, ACM on Interactive, Mobile, Wearable and Ubiquitous Technologies vol. 1 No. 4 (Year: 2017).*
Rajagopalan et al., Fall Prediction and Prevention Systems: Recent Trends, Challenges, and Future Research Directions, Nov. 1, 2017, sensors (Year: 2017).*
International Search Report and Written Opinion, International Application No. PCT/EP2019/067271, Mailed on Sep. 17, 2019.
Allen, N. et al., "The Effects of an Exercise Program on Fall Risk Factors in People with Parkinson's Disease: A Randomized Controlled Trial", Movement Disorders, vol. 25, No. 9, 2010, pp. 1217-1225.
Li, F. et al., "Tai Chi: Improving Functional Balance and Predicting Subsequent Falls in Older Persons", Medicine & Science in Sports & Exercise, 2004.
Shier, V. et al., "Implementing exercise programs to prevent falls: systematic descriptive review", Shier et al. Injury Epidemiology (2016).

* cited by examiner

SYSTEM AND METHOD THAT OPTIMIZES PHYSICAL ACTIVITY RECOMMENDATIONS BASED ON RISKS OF FALLS

CROSS-REFERENCE TO PRIOR APPLICATIONS

This application is the U.S. National Phase application under 35 U.S.C. § 371 of International Application No. PCT/EP2019/067271, filed on 27 Jun. 2019, which claims the benefit of U.S. Provisional Patent Application No. 62/691,794, filed on 29 Jun. 2018. These applications are hereby incorporated by reference herein.

TECHNICAL FIELD

Various embodiments described herein are directed generally to health care. More particularly, but not exclusively, various methods and apparatus disclosed herein relate to incorporating exercise coaching and fall prevention into a personalized activity plan by recommending activities that optimize health and build strength in users with an increased fall risk.

BACKGROUND

Falls are a significant problem, particularly for elderly people. About thirty percent of people over 65 years old fall at least once a year. The risk of a user falling at any given time can vary both in the long term (e.g. due to aging, injuries, chronic conditions, etc.) and short term (e.g. due to fatigue, lighting conditions around the person, weather conditions, the evenness of the ground, etc.).

Systems are currently available that can provide a user with an indication of their fall risk at a particular time. Activities that increase physical activity can both increase fall rates and decrease fall rates. Wearable devices provide an opportunity to track an individual's changing fall-risk and therefore offer continuously tailored guidance that optimizes the type/frequency of, and/or adherence to, various physical activities. In addition, wearable technology allows people to self-monitor their activity levels and motivate them to do more, while also giving them confidence that they are doing the correct types and amounts of activities that are suited to their abilities. However, existing wearable technology falls short with regard to the elderly population and their increased risks of falling. This is due in part to the varying psychosocial and physiological parameters associated with the elderly, as well as interactions between these parameters. Moreover, healthcare guidelines for seniors differ from those associated with the general population. For example, recommended blood pressure levels may be higher for seniors.

SUMMARY

Systems, apparatus, and techniques are described herein relating to monitoring an individual's movements and suggesting recommended activities to minimize the probability that the individual (which when benefiting from techniques described herein may be referred to as a "user") will fall while encouraging the user to be active. Put another way, techniques described herein seek to integrate balance and strength training into daily life activity. For example, integrating enhanced balance and strength training among the elderly population would reduce the rate of falls and potentially improve quality of life. A fall risk assessment (i.e. assessing the risk of a user falling at any given time) is useful for identifying elderly people that are currently at a substantial risk of falling, tailoring activities for optimizing fall prevention intervention programs and monitoring progression of the user's fall risk.

In some embodiments, a user may be provided with a list of recommended activities that are identified/selected/determined based on those activities being unlikely to raise the user's risk of fall unacceptably. In some embodiments, the list of recommended activities may be identified using a prediction model (e.g., statistical model, artificial intelligence model, machine learning model, etc.) that is updated over time as the user's risk of falling is estimated to change. In some embodiments, the prediction model may be applied once prior to providing the list of recommended activities to estimate the user's pre-activity (or "baseline") risk of fall and to identify activities to recommend to the user (e.g., that won't increase fall risk unacceptably). The prediction model may be applied again during/after the user engages in one of the recommended activities to estimate an updated risk-of-fall. A comparison of the pre-activity and updated risks-of-fall can be used to update the prediction model.

One advantage of incorporating the risk of fall calculation into the identification and recommendation of activities is that physical limitations can be compensated for over time through changes in the recommended activities. For example, if a user's risk of fall increases when a recommended activity is performed, a subsequent list of recommended activities provided to the user may include different activities. The risk of fall calculation also compensates for the differences in movements for the current user that are based on the measurements taken during the activity performed.

In various embodiments, an activity database, a plurality of sensors, and one or more computing devices may be used in combination to collect data and generate a personalized activity and exercise plan that optimizes a user's activity options while minimizing their fall risk. Due to differing guidelines for seniors compared to the general population, in some embodiments, techniques described herein can be specifically adapted for the elderly with a modified fall risk. This is not an option for existing clinic (CL) and public health service (PHS) programs. Existing CL and PHS programs cannot be specifically adapted for the elderly population with a modified fall risk characteristic. This current limitation further contributes to the increased risk of injury in elderly populations because exercise without a specific focus on fall prevention can increase both the probability and frequency of falls and injuries. The increase in injury is compounded further for unattended exercise and activity.

Embodiments described herein can be used in coaching programs for improved health, such as Public Health Service (PHS), Population Health Management (PHM), and Hospital to Home (H2H). Further uses for the current disclosure include probing the level of risk of falls within all users in a variety of health scenarios. These scenarios may include but are not limited to during pregnancy when the change in center of gravity is more difficult for the expecting mother to account for, with permanent physical disabilities (certain level of paraplegia, arthritis, Parkinson's), or temporary physical disabilities (broken leg, walking with crutches, after a surgery (e.g. joint replacement), and so forth.

In various embodiments, the prediction model may rely on any number of factors in addition to baseline and post-activity estimated risks-of-fall, such as hypotension, cognitive decline, alcohol intake, food intake (time, type), user of a rollator (rolling walker, etc.), and hypertension management. These factors can be baked into the prediction model to improve accuracy. If the impact of a given exercise/ activity recommendation on the risk of fall is too great, the system may take that into account and propose additional non-physical activity-related interventions for the user. For example, a person having very strong postprandial hypotension, which increases the person's acute risk of fall, may be recommended to have the following intervention: smaller meals and less carbohydrates to reduce the change of blood pressure after a meal.

Other embodiments include a system that takes into account the impact of exercise on the risk for other diseases, such as a cardiovascular disease (CVD) and diabetes, in its evaluation on which program to follow. For example, suppose Exercise 1 has a risk of fall variation of −30% with a corresponding CV risk variation of −4%, whereas a different type of exercise, Exercise 2, has a risk of fall variation that is also −30%, but with a corresponding CV risk variation of −10%. Based on the data points in this example, Exercise 1 and 2 have the same expected impact on the risk of fall (−30%), but different risks for CVD based on the −4% for Exercise 1 and −10% for Exercise 2 that warrant Exercise 2 being the favored exercise.

In various embodiments, a method may be provided that includes: estimating, based on one or more baseline sensor signals associated with a user, a baseline risk of fall for the user; predicting, based on a prediction model associated with the user and the baseline risk of fall, respective risks of falls associated with a plurality of candidate activities; determining or selecting, based on the predicted respective risks of falls, one or more candidate activities from the plurality of candidate activities; providing output indicative of the determined or selected one or more candidate activities to the user; receiving input from the user, wherein the input identifies one or more of the determined or selected one or more candidate activities as an exercise conducted or to be conducted by the user; estimating a subsequent risk of fall for the user based on one or more exercise sensor signals obtained during or after the user performs the candidate activity identified in the input; and updating the prediction model based on the subsequent risk of fall for the user.

In various embodiments, the method may further include: predicting, based on the updated prediction model and a subsequent baseline risk of fall, subsequent respective risks of falls associated with the plurality of candidate activities; determining or selecting, based on the subsequent respective risks of falls, one or more subsequent candidate activities from the plurality of candidate activities; and providing output indicative of the determined or selected one or more subsequent candidate activities to the user.

In various embodiments, the method may further include determining, based on one or more of the exercise sensor signals, a measure of adherence by the user with the determined or selected exercise. In various versions, estimating the subsequent risk of fall may be further based on the measure of adherence. In various embodiments, the one or more sensor signals may include a movement sensor signal indicative of movement by the user. In various embodiments, the one or more sensor signals may include a physiological sensor signal generated by a physiological sensor. In various embodiments, the physiological sensor includes one or more of a blood pressure sensor, a heartrate sensor, and a thermometer.

Other implementations may include a non-transitory computer readable storage medium storing instructions executable by a processor to perform a method such as one or more of the methods described above. Yet another implementation may include a system including memory and one or more processors operable to execute instructions, stored in the memory, to implement one or more modules or engines that, alone or collectively, perform a method such as one or more of the methods described above.

It should be appreciated that all combinations of the foregoing concepts and additional concepts described in greater detail herein are contemplated as being part of the subject matter disclosed herein. For example, all combinations of claimed subject matter appearing at the end of this disclosure are contemplated as being part of the subject matter disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating various principles of the embodiments described herein.

DETAILED DESCRIPTION

Embodiments of this disclosure relate to improving physical activity recommendations provided to a user based on the user's predicted risk(s) of falls. Techniques described herein may provide a variety of benefits, such as a higher quality of life, reduced healthcare costs, and healthier outcomes for pre-frail and frail people. Using techniques described herein it is possible to predict the impact of one or more activities on a user's risk of fall within a certain time frame, based on a variety of signals such as the user's profile (e.g., demographics, vital signs, gender, age, medical history), gathered statistics or historical data for similar users, and/or the user's current risk of fall. By running a simulation to determine how the collected data and specific activities will impact the user's risk of fall, it is possible to classify which activities should be recommended to the user.

As used herein, the term "user" may refer to any person that may use systems and/or apparatus configured with selected aspects of the present disclosure. As used herein, the term "activity" may refer to strength building exercise (e.g., weight lifting), aerobic exercise (e.g., walking, jogging, cycling, skating, hiking, etc.), balance exercise (e.g. tandem stand, one leg stand, yoga, etc.) and/or everyday actions such as taking the stairs (e.g., instead of an elevator), parking far away from a store instead of close by, standing while working, rising from a chair, household activities, etc.

Based on a user's profile and/or a variety of other signals, systems configured with selected aspects of the present disclosure may provide suggestions to the user on what exercise or activity program (e.g., list of recommended activities) to follow. For example, an effective program for a given user may be defined as when the predicted long term (greater than 10 weeks) risk of fall reduction is larger than the acute risk of fall increase during and after (2-5 days) exercise. The prediction model is updated based on the measured impact of the user's activity choices on risk of fall.

Figure 1:
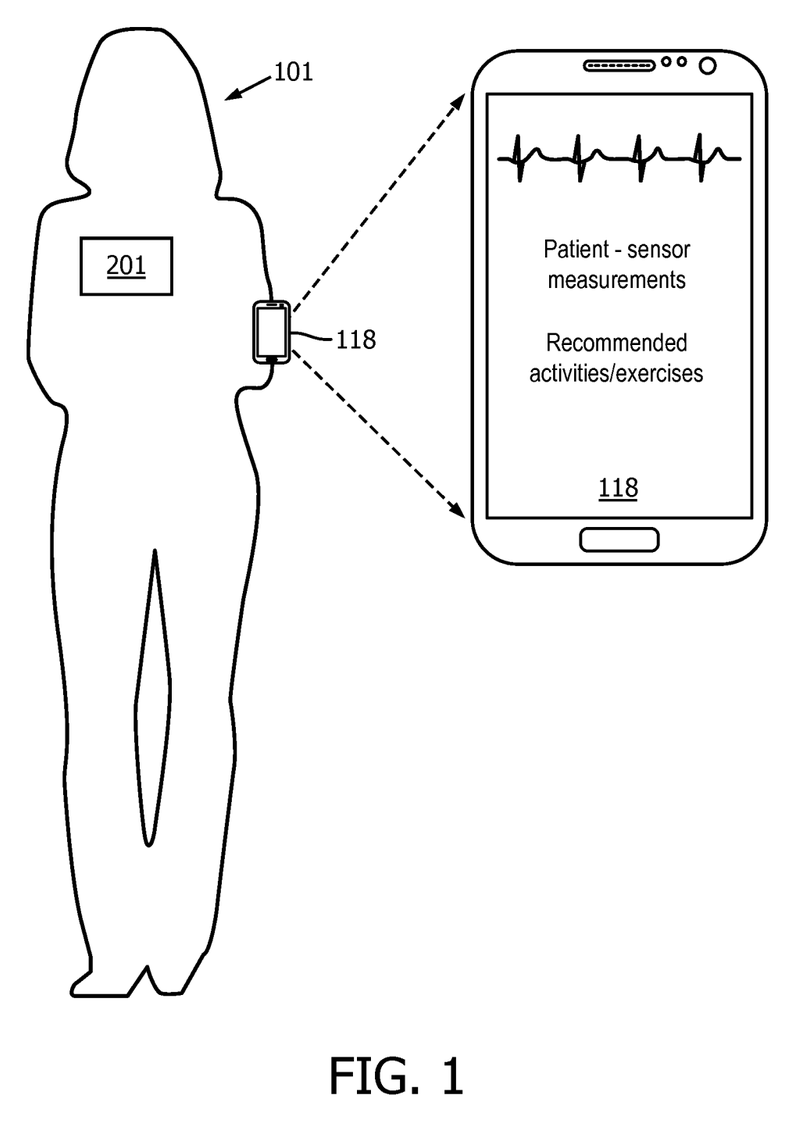
FIG. 1 schematically illustrates one example of how an apparatus configured with selected aspects of the present disclosure may be deployed on a patient, in accordance with various embodiments.

Referring now to FIG. 1, a user 101 is depicted wearing an apparatus 201 configured with selected aspects of the present disclosure. In various embodiments, user 101 may wear apparatus 201 at various locations on her body, preferably on the user's chest, but it can also be applied to her back, neck, arms, wrist, etc. In various embodiments, the apparatus 201 may be configured to communicate with one or more remote computing devices, e.g., using wired and/or wireless communication interface (237 in FIG. 2) that employs technologies such as Wi-Fi, Bluetooth, Ethernet, etc.

For example, in FIG. 1, apparatus 201 is in wireless communication with a computing device taking the form of a smart phone 118 carried by user 101. Other configurations are contemplated. In addition, while the computing device in FIG. 1 takes the form of a smart phone, computing devices may take a variety of other forms, such as laptop/desktop computers, set-top boxes, tablet computers, standalone interactive speakers, and so forth. In this example, smart phone 118 receives, from apparatus 201 via the wireless communication channel, sensor measurements. Smart phone may also determine and/or display recommended activities or activities.

Figure 2:
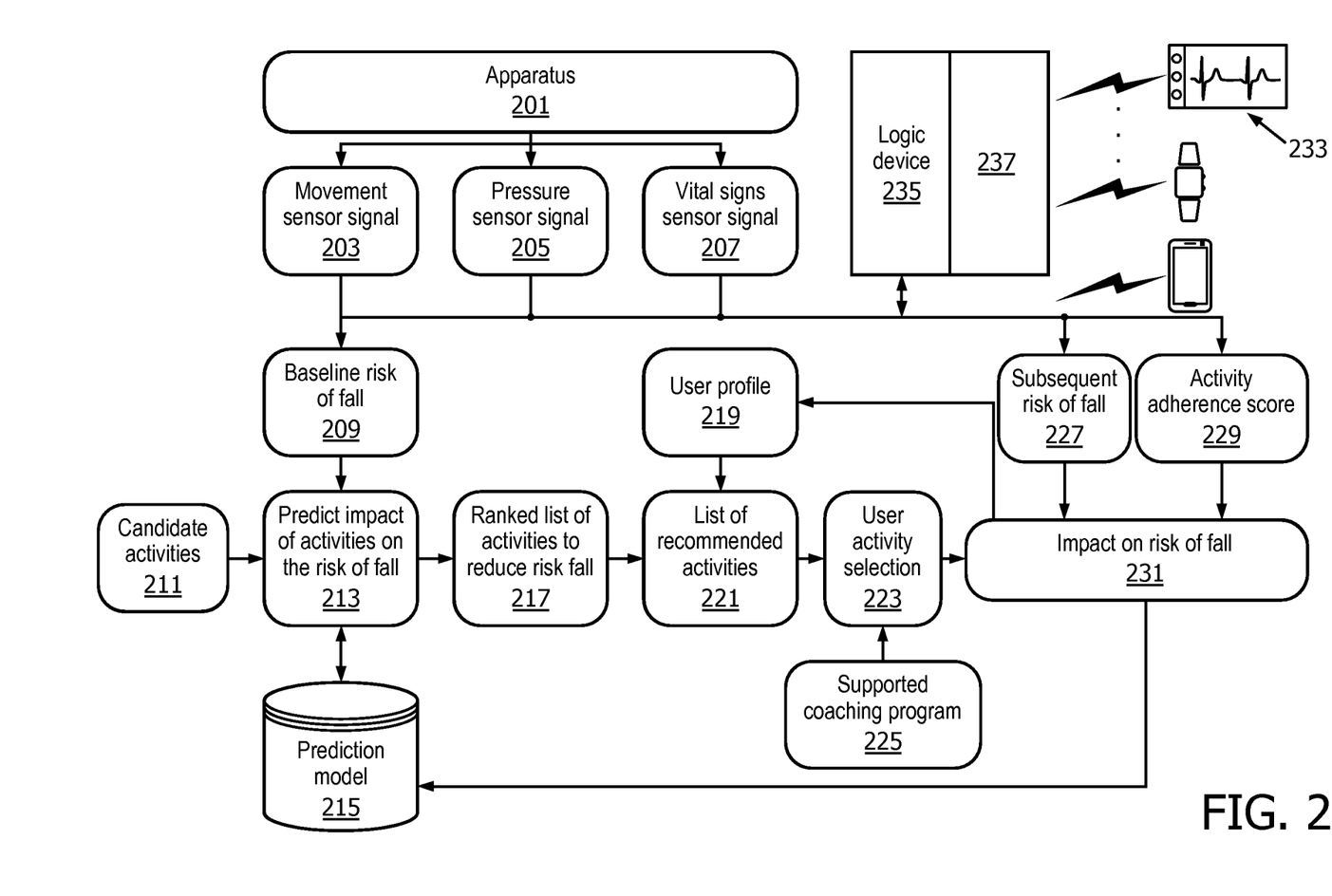
FIG. 2 illustrates an example overview regarding how the inputs signals from the sensors could be used to determine the baseline risk of fall, predict the impact of a performed exercise on the risk of fall using a prediction model, and update the prediction model, in accordance with various embodiments.

FIG. 2 schematically depicts in more detail than FIG. 1 one example of components and/or operations that may be employed in order to perform selected aspects of the present disclosure, in accordance with various embodiments. In various embodiments, a logic device 235 that may perform selected aspects of FIG. 2 may be implemented as the following non-limiting examples: one or more processors, a field-programmable gate array ("FPGA"), an application-specific integrated circuit ("ASIC"), and so forth. In some embodiments, the logic device 235 may, using wireless and/or wired communications 237, transmit various data to one or more remote computing devices 233, such as a mobile phone, smart watch, medical device, etc. These remote devices may be configured to provide audio and/or visual output indicative of the sensor measurements of the user and/or recommended activities and activities.

In FIG. 2, the apparatus 201 generates multiple sensor signals including, but not limited to, a movement sensor signal 203, a pressure sensor signal 205, and one or more vital signs sensor signals 207. In various embodiments, these sensor data may be augmented with and/or replaced by self-reporting data from users. The movement sensor signal 203 may be generated by a variety of different types of sensors, such as an accelerometer, a gyroscope, a position coordinate sensor (e.g. Global Positioning System (GPS), sensor), a magnetometer, a gyrometer, and so forth. The pressure sensor signal 205 may be generated by an assortment of varying types of sensors that may include, but are not limited to, sensors that detect walking on stairs, chair rise sensors, bed sensors, etc. The vital signs sensor signal 207 may be generated by a physiological sensor such as a blood pressure sensor, a heartrate sensor (e.g., PPG-based), a glucose sensor, a sweat sensor, a thermometer, and so forth.

The sensor signals 203-207 generated by apparatus 201 may be used to calculate a baseline risk of fall 209, a subsequent (i.e. post-activity) risk of fall 227, and an activity adherence score 229. Various techniques may be employed to calculate the baseline and subsequent risks of fall. For example, some embodiments described herein may employ techniques described in U.S. Patent Application Publication Nos. 2016/0113551 and 2016/0220153, which are incorporated herein by reference for all purposes. Additionally or alternatively, other techniques may be employed, such as application of trained machine learning models, etc. For example, historical fall data may be used to train a machine learning model to generate, based on a feature vector generated based on attributes of a particular patient, a risk of fall.

For example, baseline and/or subsequent risk of falls may be calculated by processing the determined adherence or activity type to modify a receiver operating characteristic (ROC)-curve using a Baysian network. For example a network may include different nodes, each representing a different risk factor. All nodes may contribute to the root node, which holds the fall risk. There may be different types of risks. These may be reflected in the hierarchy of the tree. For example, sensor data, movement data, and/or adherence data described herein may be modelled. History of falls and/or chronic disease data may also be reflected. The various links or arrows in a network may hold a conditional probability or probabilities for the values of the arriving node given the value(s) of the departing node(s). In this way, the probability of the fall risk is expressed by the joint of the factors represented by the other nodes. The leaf nodes are assigned with a default value, which is the prior probability (the most commonly encountered value for this population in practice). When the value is known, this is assigned to the node replacing the default. It can also happen that the value of an intermediate node is known. Then this value is assigned (as well). As a consequence of such a value change, the value at the other nodes will also change. This update happens according to the given conditional probabilities. A Bayesian Network may be designed with the arrows in opposite direction, i.e. reversing the "cause" and "effect" nature of the nodes. This helps to reduce the complexity of the network (leading to faster updating) as well as helping to arrive at the prior and conditional probability values. Other mechanisms as described herein may be used.

After the baseline risk statistic 209 is calculated, it may be used at block 213 to predict risks of falls for a plurality of candidate activities 211. In particular, the prediction of block 213 may rely on a prediction model 215. Prediction model 215 may take various forms, such as a statistical model and/or an artificial intelligence model (e.g., Bayesian network model described above). Various artificial intelligence models may be employed as part of prediction model 215, including but not limited to neural networks, support vector machines, discriminant analysis classifiers, Gaussian Naïve Bayes classifiers, Kernel Naïve Bayes classifiers, decision tree classifiers, a decision tree ensemble using, for instance, AdaBoost, a decision tree ensemble using bootstrap aggregation, a decision tree ensemble using random under sampling, and so forth.

In order to build the prediction model 215, in some embodiments, different sub-models (one for each signal/movement event class) can be combined which are trained on different features in a multiple classifier system where each sub-model votes to obtain a predictor score. The general idea of combining classifiers can be summarized by the use of a methodology to create an ensemble of learners and to produce a final decision given the outputs of those learners. Moreover, creating a separate model for each event class allows for the production of a risk score, e.g., in the case that some events are missing (e.g. a subject did not monitor a certain vital sign). The capability of dealing with missing events is a beneficial feature because event classes can differ per subject. In case of missing events, the other sub-models of the multiple classifier system may continue to produce a fall-risk score. In some embodiments, falls may be detected automatically. Fallen users may be asked to enter falls status (e.g. confirm fall, cause of fall, environment in which the fall took place, falls severity) to obtain labels for the models described previously. In various embodiments, those models can be tested with new incoming data and re-trained if needed.

Based on candidate activity fall risks predicted at block 213, at block 217, a list of activities (which may or may not be ranked) is determined or selected that reduces a risk of fall to the user. For example, in some embodiments, the candidate activities may be ranked by their predicted fall risks, e.g., with the activities having the lowest risk of fall being ranked highest. In various embodiments, at block 221, a subset of the ranked list of activities generated at block 217 may be determined or selected and provided as a list of recommended activities to the user. For example, the top n activities generated at block 217 may be determined or selected, wherein n is an integer greater than one. Subsequently, at block 223, the user, with the optional aid of a supported coaching program 225, makes or receives a selection of an activity to perform.

The sensor signals 203-207 may continue to be generated while the user engages in the activity he or she received or selected at block 223. At block 227, these subsequent sensor signals may be used, e.g., by logic device 235, to estimate a subsequent risk of fall of the user during and/or after he/she engages in the determined or selected activity. In some embodiments, at block 231, the subsequent risk of fall estimated at block 227 may be used in conjunction with an activity adherence score 229 (and in some cases with the determined or selected user activity) to determine an impact each of these factors has on the user's risk of fall, e.g., relative to the previously-estimated baseline risk of fall and/or relative to the predicted risk of fall for the determined or selected activity. In some embodiments, the activity adherence score 229 may be measured based on comparing the determined or selected activity to the sensor signals 203-207 obtained while the actual activity is being performed. The activity adherence score may convey how closely the actual movements of the user are to the determined or selected exercise.

In various embodiments, the impact on the risk of fall calculated at block 231 may be used to update the prediction model 215. By updating prediction model 215 as part of an overall feedback loop, prediction model 215 can then be used to generate updated predictions of risks of falls for the candidate activities 211. These in turn are usable to generate an updated list of recommended activities 221 for the user to perform or select from. In various embodiments, prediction model 215 may be associated with a specific user and/or with a population of users. For example, suppose a user engages in a particular recommended activity that unexpectedly raises the user's risk of fall. That user's individual prediction model 215, or a prediction model 215 associated with a population of similar users, may be updated so that the particular activity is less likely to be recommended to that user and/or to other users of the population of users.

In some implementations, a supported coaching program 225 may provide output that is influenced based on a user's ongoing risk of fall. When prediction model 215 is updated, in some embodiments, content that is used to provide coaching messages may also be updated. For example, a person at low-risk of falling may be provided with a coaching message that recommends relatively kinetic activities such as pacing while talking on the phone, bouncing on an exercise ball while watching television, etc. If it is determined over time, however, that engaging in these activities increases the user's risk of fall unacceptably, then in various embodiments, these recommended activities may be replaced with less ambitious activities, such as placing items on lower shelves to require the user to bend down to get them, keeping a remote control on top of a television (to force the user to go get it), etc. Also, when a user's risk of fall increases, various safety messages may be included with the coaching, such as "don't forget to take your walking aid with you."

Figure 3:
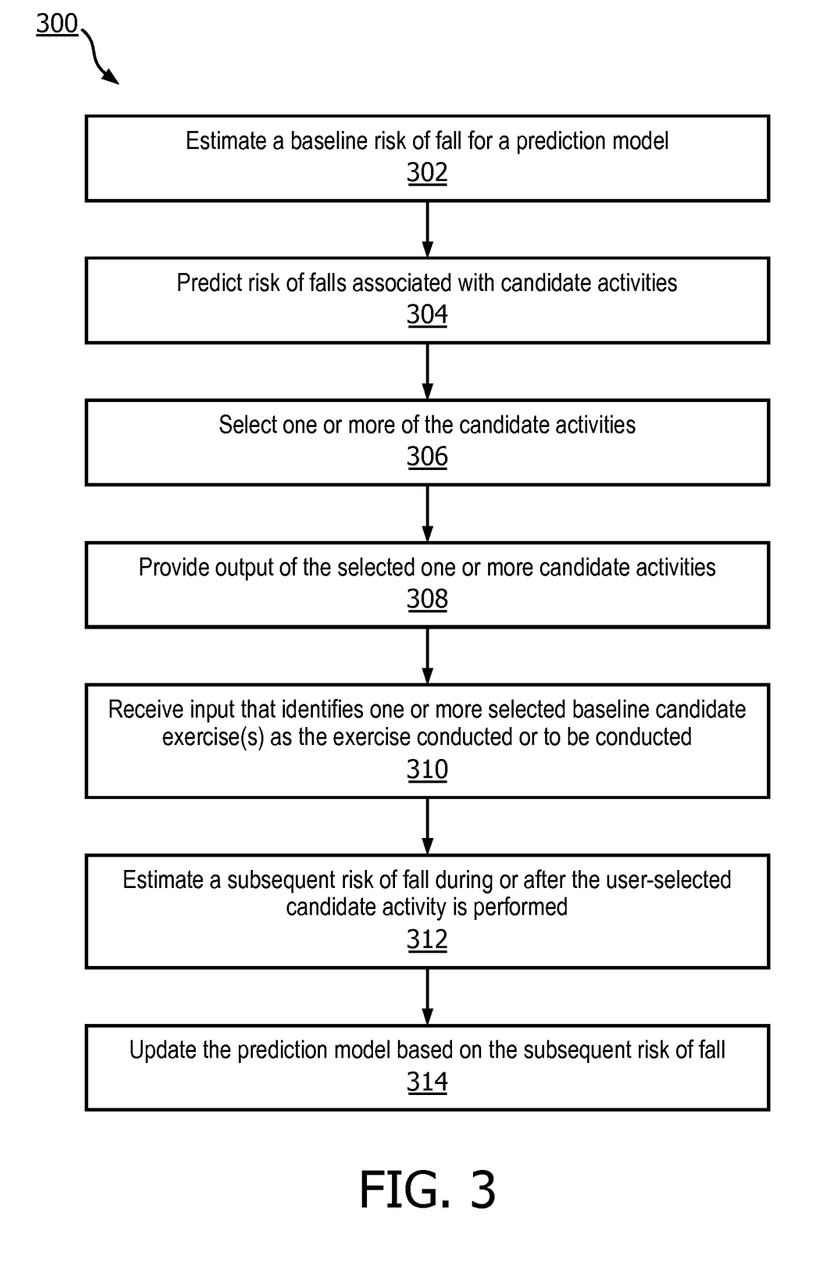
FIG. 3 schematically illustrates an example method for practicing selected aspects of the present disclosure.

FIG. 3 depicts an example method 300 for practicing selected aspects of the present disclosure, in accordance with various embodiments. For convenience, the operations of the flow chart are described with reference to a system that performs the operations. This system may include various components of various computer systems, including logic device 235. Moreover, while operations of method 300 are shown in a particular order, this is not meant to be limiting. One or more operations may be reordered, omitted or added.

At block 302, the system may estimate a baseline risk of fall, e.g., based on one or more sensor signals (e.g., 203-207) and/or demographics of the user, similar to block 209 of FIG. 2. At block 304, the system may predict the risk of falls associated with a plurality of candidate activities, similar to block 213 of FIG. 2. For example, the system may calculate an impact each candidate activity would have on the baseline risk of fall estimated at block 302. Based on the predicted risks of falls associated with the candidate activities, at block 306, the system may select a ranked list of activities. At block 308, the system may select from the ranked list of activities, and provide as output (e.g., as a list of selectable elements or a list of determined elements), one or more activities that, for instance, satisfy a risk of fall threshold, the top n activities having the least impact on risk of fall, etc.

At block 310, the system receives input from the user or the system itself that selects one of the activities presented as output at block 308. For example, a user operating a smart phone may, at block 308, be presented with a list of selectable graphical elements and/or determined elements, each corresponding to a recommended activity. At block 310, the user may tap on a graphical element to indicate that the user intends to engage in the recommended activity. Additionally or alternatively, in some embodiments, the user may not provide input indicating which activity the user will engage in. Instead, the user may simply start engaging in the activity, and one or more activity (or exercise) classifiers may analyze movement sensor signals 203 to generate output indicative of the detected activity.

At block 312, a subsequent risk of fall during or after the determined or selected candidate activity may be calculated or estimated. A subsequent risk of fall may include determining, based on one or more exercise sensor signals, a measure of adherence to the exercise, and/or trained machine learning models. A measure of adherence to the exercise may be calculated using movement data, vital signs data, a score determined by comparing determined or selected activity to the sensor signals obtained while the actual activity is being performed, and/or a score determined by comparing actual movement data against anticipated movement data associated with a determined or selected activity. Machine learning models may be used, for example, with historical fall data, where historical fall data may be used to train a machine learning model to generate, based on a feature vector generated based on attributes of a particular patient, a risk or updated risk of fall.

In various embodiments, a subsequent risk of fall may be calculated using the impact on the risk of fall (for example, the risk of fall calculation described herein), where a risk of fall may be used to update a prediction model in block 314 (e.g., prediction model 215). By updating a prediction model as part of an overall feedback loop, a prediction model can then be used to generate updated predictions of risks of falls for a current and/or subsequent activity. A prediction model may be used to generate an updated list of recommended activities for the user to select from and/or for the user to perform. In various embodiments, a prediction model may be associated with a specific user and/or with a population of users. For example, suppose a user engages in a particular recommended activity that unexpectedly raises the user's risk of fall. That user's individual prediction model, or a prediction model associated with a population of similar users, may be updated so that the particular activity is less likely to be recommended to that user and/or to other users of the population of users.

Figure 4:
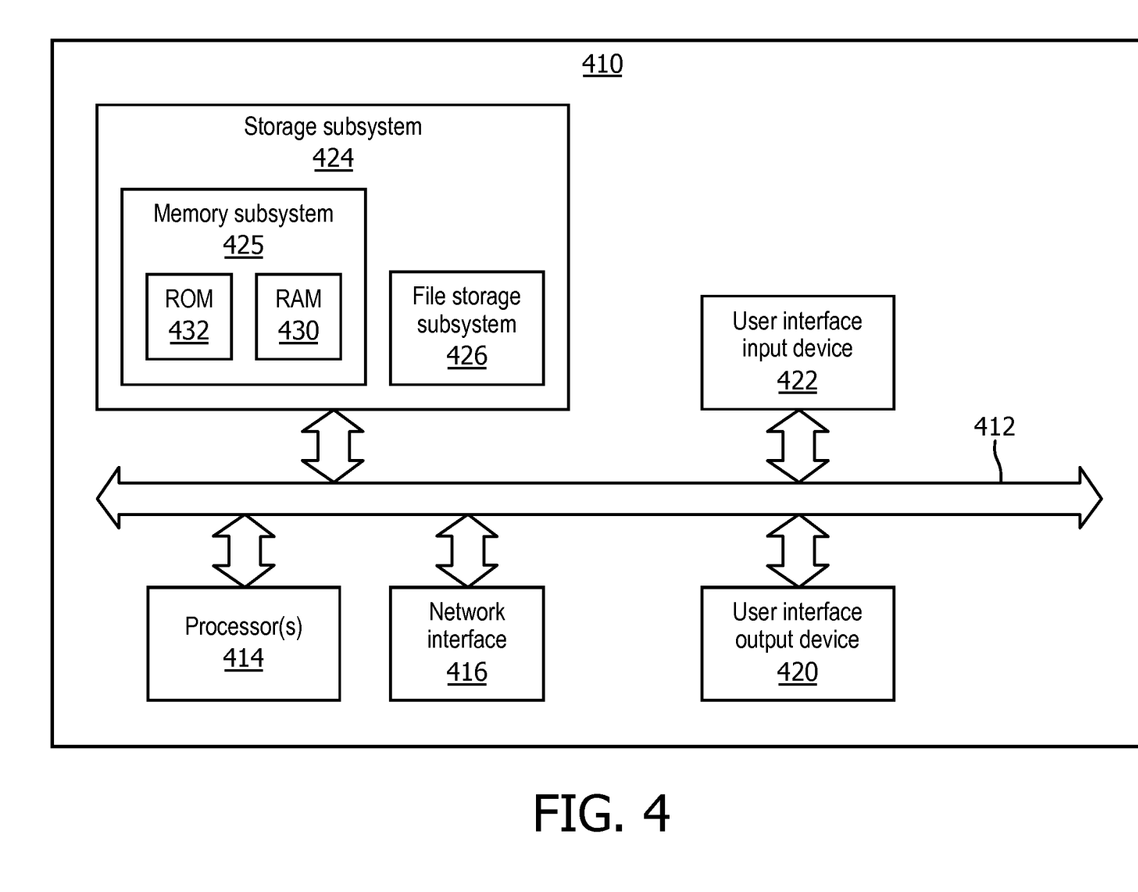
FIG. 4 illustrates an example computing architecture.

FIG. 4 is a block diagram of an example computing device 410 that may optionally be utilized to perform one or more aspects of techniques described herein. In some implementations, one or more of a client computing device, user-controlled resources engine 130, and/or other component(s) may comprise one or more components of the example computing device 410.

Computing device 410 typically includes at least one processor 414 which communicates with a number of peripheral devices via bus subsystem 412. These peripheral devices may include a storage subsystem 424, including, for example, a memory subsystem 425 and a file storage subsystem 426, user interface output devices 420, user interface input devices 422, and a network interface subsystem 416. The input and output devices allow user interaction with computing device 410. Network interface subsystem 416 provides an interface to outside networks and is coupled to corresponding interface devices in other computing devices.

User interface input devices 422 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computing device 410 or onto a communication network.

User interface output devices 420 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computing device 410 to the user or to another machine or computing device.

Storage subsystem 424 stores programming and data constructs that provide the functionality of some or all of the modules described herein. For example, the storage subsystem 424 may include the logic to perform selected aspects of the method of FIG. 3, as well as to implement various components depicted in FIGS. 1 and 2.

These software modules are generally executed by processor 414 alone or in combination with other processors. Memory 425 used in the storage subsystem 424 can include a number of memories including a main random access memory (RAM) 430 for storage of instructions and data during program execution and a read only memory (ROM) 432 in which fixed instructions are stored. A file storage subsystem 426 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 426 in the storage subsystem 424, or in other machines accessible by the processor(s) 414.

Bus subsystem 412 provides a mechanism for letting the various components and subsystems of computing device 410 communicate with each other as intended. Although bus subsystem 412 is shown schematically as a single bus, alternative implementations of the bus subsystem may use multiple busses.

Computing device 410 can be of varying types including a workstation, server, computing cluster, blade server, server farm, or any other data processing system or computing device. Due to the ever-changing nature of computers and networks, the description of computing device 410 depicted in FIG. 4 is intended only as a specific example for purposes of illustrating some implementations. Many other configurations of computing device 410 are possible having more or fewer components than the computing device depicted in FIG. 4.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

What is claimed is:

1. A method implemented using one or more processors, comprising:
    estimating, based on one or more baseline sensor signals associated with a user, a baseline risk of fall for the user;
    predicting, based on a Bayesian neural network prediction model associated with the user and the baseline risk of fall, respective risks of falls associated with a plurality of candidate activities,
        wherein the Bayesian neural network prediction model comprises two or more sub-models trained on different event classes in a multiple classifier system, wherein the different event classes relate to one or more exercise sensor signals and/or movements, and
        wherein each sub-model comprises a root node and one or more leaf nodes, each leaf node assigned an independent default value associated with probability of a fall;
        wherein each of the two or more sub-models votes to determine a predictor score;
    determining, based on the predicted respective risks of falls, one or more candidate activities from the plurality of candidate activities;
    providing output indicative of the determined one or more candidate activities to the user;
receiving input from the user, wherein the input identifies one or more of the determined one or more candidate activities as an exercise conducted or to be conducted by the user;
    estimating a subsequent risk of fall for the user based on the one or more exercise sensor signals obtained during or after the user performs the candidate activity identified in the input and the predictor score; and
    updating the root nodes of the Bayesian neural network sub-models based on the subsequent risk of fall for the user.

2. The method of claim 1, further comprising:
    predicting, based on the updated neural network prediction model and a subsequent baseline risk of fall, subsequent respective risks of falls associated with the plurality of candidate activities;
    determining, based on the subsequent respective risks of falls, one or more subsequent candidate activities from the plurality of candidate activities;
    providing output indicative of the determined one or more subsequent candidate activities to the user.

3. The method of claim 1, further comprising determining, based on one or more of the exercise sensor signals, a measure of adherence by the user with the determined exercise.

4. The method of claim 3, wherein estimating the subsequent risk of fall is further based on the measure of adherence.

5. The method of claim 1, wherein the one or more baseline sensor signals include a movement sensor signal indicative of movement by the user.

6. The method of claim 1, wherein the one or more baseline sensor signals include a physiological sensor signal generated by a physiological sensor.

7. The method of claim 6, wherein the physiological sensor includes one or more of a blood pressure sensor, a heartrate sensor, and a thermometer.

8. A system comprising one or more processors and memory operably coupled with the one or more processors, wherein the memory stores instructions that, in response to execution of the instructions by one or more processors, cause the one or more processors to perform the following operations:
- estimating, based on one or more baseline sensor signals associated with a user, a baseline risk of fall for the user;
- predicting, based on a Bayesian neural network prediction model and the baseline risk of fall, respective risks of falls associated with a plurality of candidate activities,
  - wherein the Bayesian neural network prediction model comprises two or more sub-models trained on different event classes in a multiple classifier system,
    - wherein each sub-model comprises a root node and one or more leaf nodes, each leaf node assigned an independent default value associate with probability of a fall;
  - wherein the different event classes relate to one or more exercise sensor signals and/or movements, and
  - wherein each of the two or more sub-models votes to determine a predictor score;
- determining, based on the predicted respective risks of falls, one or more candidate activities from the plurality of candidate activities;
- providing output indicative of the determined one or more candidate activities to the user;
- receiving input from the user, wherein the input identifies one or more of the determined one or more candidate activities as an exercise conducted or to be conducted by the user;
- estimating a subsequent risk of fall for the user based on the one or more exercise sensor signals obtained during or after the user performs the candidate activity identified in the input and the predictor score; and
- updating the root nodes of the Bayesian neural network sub-models based on the subsequent risk of fall for the user.

9. The system of claim 8, further comprising:
- predicting, based on the updated neural network prediction model and a subsequent baseline risk of fall, subsequent respective risks of falls associated with the plurality of candidate activities;
- determining, based on the subsequent respective risks of falls, one or more subsequent candidate activities from the plurality of candidate activities;
- providing output indicative of the determined one or more subsequent candidate activities to the user.

10. The system of claim 8, further comprising determining, based on one or more of the exercise sensor signals, a measure of adherence by the user with the determined exercise.

11. The system of claim 10, wherein estimating the subsequent risk of fall is further based on the measure of adherence.

12. The system of claim 8, wherein the one or more sensor signals include a movement sensor signal indicative of movement by the user.

13. The system of claim 8, wherein the one or more sensor signals include a physiological sensor signal generated by a physiological sensor.

14. The system of claim 13, wherein the physiological sensor includes one or more of a blood pressure sensor, a heartrate sensor, and a thermometer.

15. At least one non-transitory computer-readable medium comprising instructions that, in response to execution of the instructions by one or more processors, cause the one or more processors to perform the following operations:
- estimating, based on one or more baseline sensor signals associated with a user, a baseline risk of fall for the user;
- predicting, based on a Bayesian neural network prediction model associated with the user and the baseline risk of fall, respective risks of falls associated with a plurality of candidate activities,
  - wherein the Bayesian neural network prediction model comprises two or more sub-models trained on different event classes in a multiple classifier system,
    - wherein each sub-model comprises a root node and one or more leaf nodes, each leaf node assigned an independent default value associated with probability of a fall;
  - wherein the different event classes relate to one or more exercise sensor signals and/or movements, and
  - wherein each of the two or more sub-models votes to determine a predictor score;
- determining, based on the predicted respective risks of falls, one or more candidate activities from the plurality of candidate activities;
- providing output indicative of the determined one or more candidate activities to the user;
- receiving input from the user, wherein the input identifies one or more of the determined one or more candidate activities as an exercise conducted or to be conducted by the user;
- estimating a subsequent risk of fall for the user based on the one or more exercise sensor signals obtained during or after the user performs the candidate activity identified in the input and the predictor score; and
- updating the root nodes of the Bayesian neural network sub-models based on the subsequent risk of fall for the user.

* * * * *